(12) United States Patent
Porter et al.

(10) Patent No.: US 6,198,277 B1
(45) Date of Patent: Mar. 6, 2001

(54) SENSOR MODULE FOR USE IN SYSTEM FOR INSPECTING IN-SERVICE GAS DISTRIBUTION MAINS

(75) Inventors: Patrick Porter; Gerry Pittard, both of Houston, TX (US); Kiran M. Kothari, Hoffman Estates, IL (US); Philippe Rave, Paris (FR)

(73) Assignee: Gas Research Institute, Chicago, IL (US)

( * ) Notice: Subject to any disclaimer, the term of this patent is extended or adjusted under 35 U.S.C. 154(b) by 0 days.

(21) Appl. No.: 09/105,834

(22) Filed: Jun. 26, 1998

Related U.S. Application Data

(60) Provisional application No. 60/050,892, filed on Jun. 26, 1997.

(51) Int. Cl.$^7$ .......................... G01R 33/12; G01N 27/82
(52) U.S. Cl. ........................ 324/220; 324/240; 324/242
(58) Field of Search ........................... 324/219, 220, 324/221, 238, 239, 240, 242, 243, 226

(56) References Cited

U.S. PATENT DOCUMENTS

| | | |
|---|---|---|
| 2,963,644 | * 12/1960 | Nuttall .............................. 324/220 |
| 3,949,292 | 4/1976 | Beaver et al. . |
| 4,649,948 | 3/1987 | Hudson . |
| 5,025,670 | 6/1991 | McNulty et al. . |
| 5,084,764 | 1/1992 | Day . |
| 5,105,876 | 4/1992 | Burack et al. . |
| 5,454,276 | 10/1995 | Wernicke . |
| 5,571,977 | 11/1996 | Kipp . |
| 5,612,499 | 3/1997 | Andrew et al. . |
| 5,660,202 | 8/1997 | Rush, Jr. et al. . |

FOREIGN PATENT DOCUMENTS

| | | |
|---|---|---|
| 523880 | 1/1993 | (EP) . |
| 606999 | 7/1994 | (EP) . |
| 2301187 | 11/1976 | (GB) . |
| 63-305242 | 12/1988 | (JP) . |

* cited by examiner

Primary Examiner—Walter E. Snow
(74) Attorney, Agent, or Firm—Pauley Petersen Kinne & Fejer

(57) ABSTRACT

A system for inspecting in-service gas distribution mains is disclosed. Coiled tubing technology and magnetic flux leakage (MFL) technology are integrated to produce a new inspection system for low pressure, in-service distribution pipelines. The coiled tubing provides the means by which an inspection module employing MFL technology is inserted into, moved through, and removed from an in-service pipeline. A portable inspection system can thereby be moved to a desired location on a trailer. The sensor module comprises a plurality of magnet assemblies each having a Magnet N out, a Magnet S out and a magnet core, the magnet assemblies being conical in shape and being arranged into a circular array. The magnet array diameter is smaller than that of a pipe to be inspected, thus defining a radial air gap. The magnet array being constructed and arranged to provide a magnetic circuit having sufficient strength so as to be operable through the radial air gap. A centering mechanism is constructed and arranged to maintain the sensor module in concentric relation with the pipe to be inspected. This array provides an efficient method of packing the magnets to generate the very powerful magnetic field desired. The conical shape of the magnets in this assembly permits the unit to negotiate tighter bends than would be possible with a cylindrical assembly. The centering mechanism permits product bypass and minimizes removal of surface debris.

18 Claims, 17 Drawing Sheets

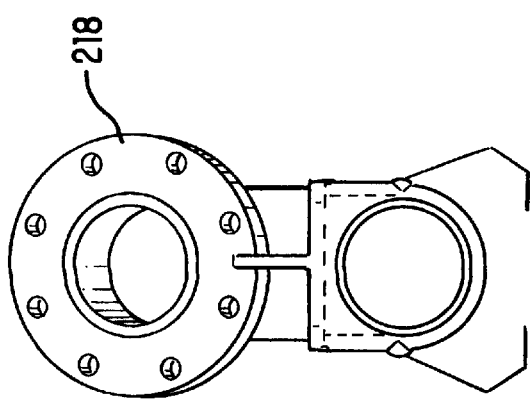
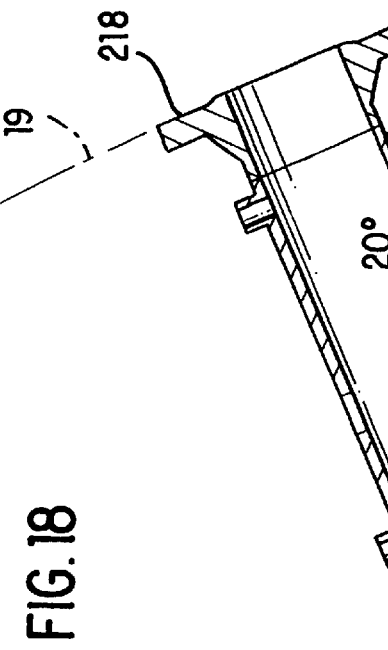
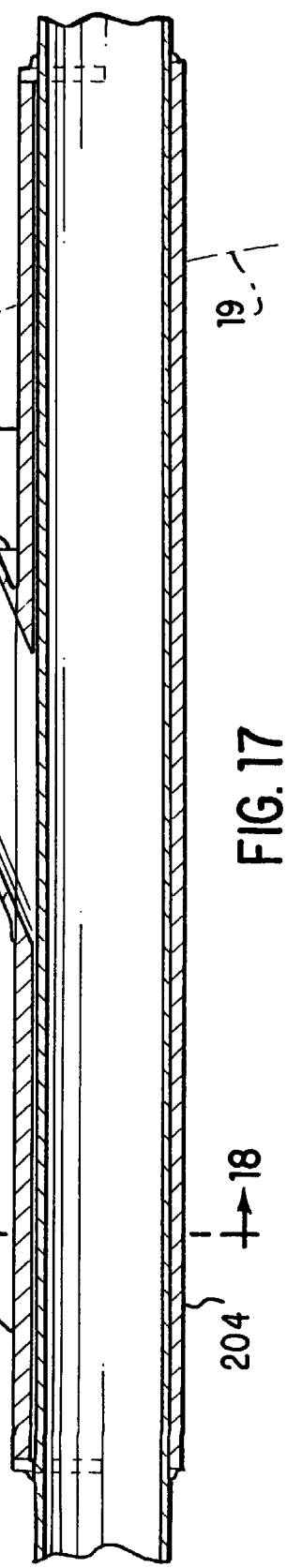
FIG. 18
FIG. 19
FIG. 17

SENSOR MODULE FOR USE IN SYSTEM FOR INSPECTING IN-SERVICE GAS DISTRIBUTION MAINS

CROSS-REFERENCE TO RELATED APPLICATION

This application claims the benefit of U.S. Provisional Patent Application Ser. No. 60/050,892, filed Jun. 26, 1997.

BACKGROUND OF THE INVENTION

1. Field of the Invention

This invention relates to a system for inspecting low pressure, low flow distribution pipelines for defects in structural integrity used in the natural gas pipeline distribution field.

2. Description of Prior Art

There are hundreds of thousands of miles of low pressure, low flow steel distribution pipelines currently in operation. All pipelines are prone to time dependent defects, such as corrosion, which can reduce safety, undermine security of service and threaten the environment if failure occurs. Prudent operators recognized the need to inspect these pipelines to ensure that affected locations are repaired or replaced before failure occurs.

In the mid-1960's, systems were developed to inspect high pressure transmission pipelines. These inspection devices are commonly referred to as "pigs" ("intelligent pigs," "smart pigs"). While there are several technologies currently used for this inspection application, the first developed, and still the most common, is that of Magnetic Flux Leakage (MFL). However, these have heretofore only been used on a frequent and reliable basis in high-pressure environments. Thus, there has been a need for an inspection system developed for low pressure distribution pipelines that exploits MFL technology.

Traditional pipeline inspection tools are free swimming devices that travel through the pipeline with the flowing product. A seal is formed to the wall of the pipeline by flexible cups attached to the tool. A differential pressure across this sealed cup creates the force preferred to propel the tool. Magnetic flux leakage inspection tools generally have two or more segments coupled together by a flexible joint.

The MFL inspection technique is well established and generally easy to apply in high pressure applications. It comprises inducing a high level magnetic field into the wall of the pipeline under inspection and scanning the inside surface with a magnetic sensor to detect variations in the magnetic field caused by wall thinning defects or other imperfections or features which change the expected magnetic properties of the material.

A typical MFL inspection tool contains a magnetic section to induce a magnetic field into the pipe wall. This section can comprise either permanent magnets or electromagnets. The magnetic poles (North/South) are separated axially along the pipe and connected to the pipe by hard metallic pole pieces or flexible wire brushes. The pipe between the poles forms part of the magnetic circuit and can be saturated with magnetic field. Sensors are mounted mid-way between the poles and radiate circumferentially around the pipe. These sensors scan the inside wall of the pipe as the tool is moved through the pipeline.

Another module on the tool contains electronic systems to process and store information acquired by the sensor. Additional modules contain batteries and control systems preferred for tool operation.

Low pressure, low flow distribution pipelines present a unique challenge to the application of this technology. The pressure and flow are not adequate to propel the tool. The inspection system should operate in an in-service pipeline without disrupting flow. The system should minimize wall contact to reduce contamination of the product with debris or deposits which may reside on the pipe wall. The system should be small and flexible to negotiate minor changes in bore and normal pipe bends. The system should operate at very low power levels in order to be certified for gas operation. The system should provide the method of gaining access to the pipeline to be inspected under live conditions; inserting the inspection device into the pipeline; propelling the inspection module through the pipeline and withdrawing the module at a single location. The system should consider bi-directional operation from a single entry point and be portable (trailer mounted) to allow operation in congested city areas. The inspection should be fast and the inspection data available in real time.

Thus, a problem associated with systems for inspecting in-service gas distribution mains that precede the present invention is that many of them are not capable of self-propulsion, as the pressure and flow are inadequate to propel the tool.

Another problem associated with systems for inspecting in-service gas distribution mains that precede the present invention is that many of them could disrupt the flow of the product in the pipeline in this application.

Yet a further problem associated with systems for inspecting in-service gas distribution mains that precede the present invention is that many of them contact the pipe wall excessively, thereby causing contamination of the product with debris or deposits which may reside on the pipe wall.

Still another problem associated with systems for inspecting in-service gas distribution mains that precede the present invention is that many of them are not small and flexible enough to be inserted into the main through the off-take.

An even further problem associated with systems for inspecting in-service gas distribution mains that precede the present invention is that many of them do not operate at sufficiently low power levels to be certified for gas operation.

Another problem associated with systems for inspecting in-service gas distribution mains that precede the present invention is that many of them do not provide a method of gaining access to the pipeline to be inspected under live conditions.

Yet another problem associated with systems for inspecting in-service gas distribution mains that precede the present invention is that many of them are not insertable into the pipeline through a side off-take.

Still a further problem associated with systems for inspecting in-service gas distribution mains that precede the present invention is that many of them comprise an inspection module which cannot be propelled through the pipeline and withdrawn from the pipeline at a single location.

Another problem associated with systems for inspecting in-service gas distribution mains that precede the present invention is that many of them do not facilitate bi-directional operation from a single entry point in the pipeline.

A further problem associated with systems for inspecting in-service gas distribution mains that precede the present invention is that many of them are not portable to allow operation in congested city areas.

An additional problem associated with systems for inspecting in-service gas distribution mains that precede the present invention is that many of them do not provide for a rapid inspection.

Yet another problem associated with systems for inspecting in-service gas distribution mains that precede the present invention is that many of them do not furnish inspection data available in real time.

For the foregoing reasons, there has been defined a long felt and unsolved need for a system for inspecting in-service gas distribution mains that can be propelled through a low pressure, low flow pipeline and yet can provide real time, reliable data as to the condition of that pipeline.

In contrast to the foregoing, the present invention constitutes a system for inspecting in-service gas distribution mains that seeks to overcome the problems discussed above, while at the same time providing a simple, easily constructed apparatus that is readily adapted to a variety of applications.

SUMMARY OF THE INVENTION

A system for inspecting in-service gas distribution mains is disclosed which integrates two existing technologies to produce a new inspection system for low pressure, low flow, in-service distribution pipelines. These technologies are (1) coiled tubing and (2) Magnetic Flux Leakage (MFL) analysis. The coiled tubing provides the means by which an inspection module employing MFL technology can be inserted into, moved through, and removed from an in-service pipeline, thereby providing an operator with detailed information on the condition of the pipeline.

The overall inspection system comprises four main elements: (1) the MFL/Sensor module; (2) means for data acquisition and display; (3) a delivery system; and (4) insertion techniques and hardware. Each of these elements will be described in such clear, concise terms as to enable one having ordinary skill in the art to practice the invention herein.

It is therefore an object of the present invention to provide a system for inspecting in-service gas distribution mains that is capable of self-propulsion, as the pressure and flow are inadequate to propel the tool.

Still another object of the present invention is to provide a system for inspecting in-service gas distribution mains that will not disrupt the flow of the product in the pipeline.

Yet another object of the present invention is to provide a system for inspecting in-service gas distribution mains that will not contact the pipe wall excessively, thereby causing contamination of the product with debris or deposits which may reside on the pipe wall.

A further object of the present invention is to provide a system for inspecting in-service gas distribution mains that is small and flexible to negotiate minor changes in bore and normal pipe bends.

An even further object of the present invention is to provide a system for inspecting in-service gas distribution mains that operates at sufficiently low power levels to be certified for gas operation.

An additional object of the present invention is to provide a system for inspecting in-service gas distribution mains that provides a method of gaining access to the pipeline to be inspected under live conditions.

Still another object of the present invention is to provide a system for inspecting in-service gas distribution mains that is insertable into the pipeline.

Yet another object of the present invention is to provide a system for inspecting in-service gas distribution mains having an inspection module thereof that can be propelled through the pipeline and withdrawn from the pipeline at a single location.

A further object of the present invention is to provide a system for inspecting in-service gas distribution mains that facilitates bi-directional operation from a single entry point in the pipeline.

An even further object of the present invention is to provide a system for inspecting in-service gas distribution mains that is portable to allow operation in congested city areas.

An additional object of the present invention is to provide a system for inspecting in-service gas distribution mains that provides for a rapid inspection.

Yet another object of the present invention is to provide a system for inspecting in-service gas distribution mains that furnishes inspection data available in real time.

These and other objects, advantages and features of the present invention will be apparent from the detailed description that follows.

DESCRIPTION OF THE DRAWINGS

In the detailed description that follows, reference will be made to the following figures:

FIG. 17 is a side, cut-away view illustrating MFL left-in-place hardware as used in a preferred embodiment of a system for inspecting in-service gas distribution mains.

FIG. 18 is a cross-sectional view of the apparatus shown in FIG. 17 as seen along the line 18—18.

FIG. 19 is a cross-sectional view of the apparatus shown in FIG. 17 as seen along the line 19—19.

DETAILED DESCRIPTION OF THE PREFERRED EMBODIMENTS

Figure 1:
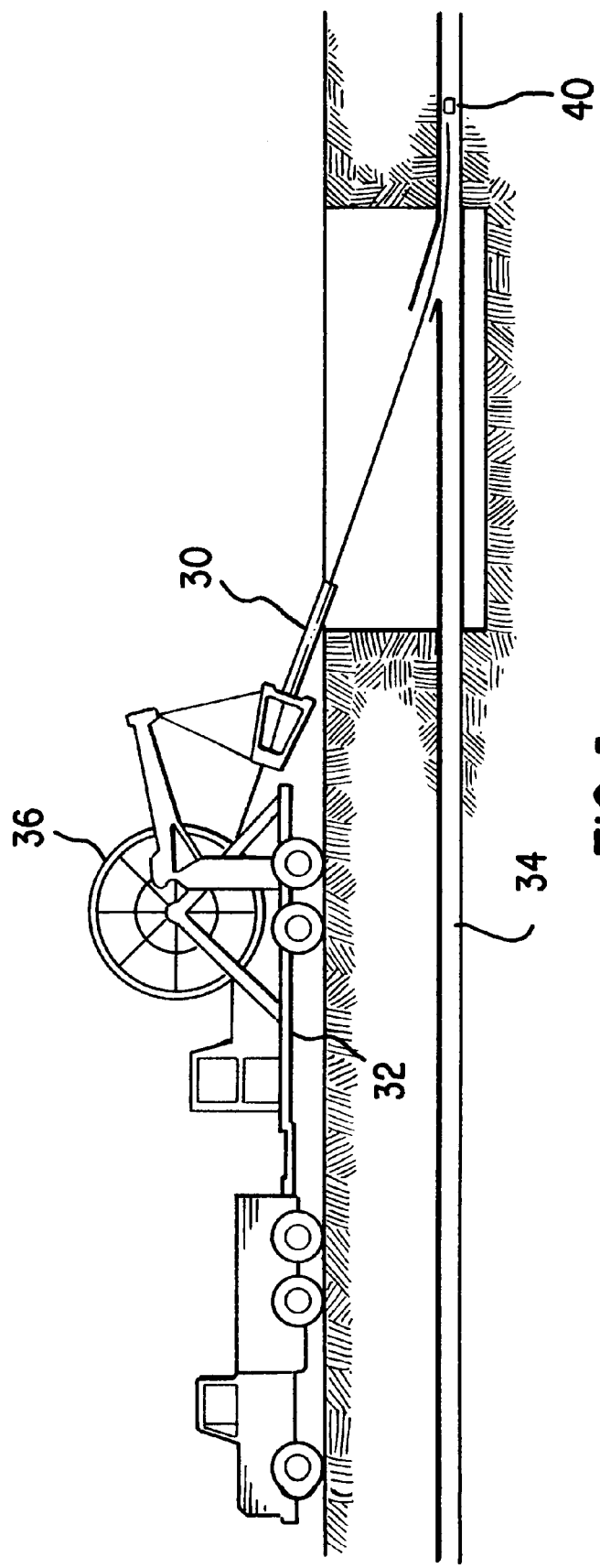
FIG. 1 is a side, perspective view illustrating a preferred embodiment of a system for inspecting in-service gas distribution mains.

FIG. 1 illustrates a first embodiment of the system for inspecting in-service gas distribution mains. As shown, coiled tubing technology and magnetic flux leakage (MFL) technology are integrated to produce a new inspection system for low pressure, low flow, in-service distribution pipelines. The coiled tubing provides the means by which an inspection module employing MFL technology is inserted into, moved through, and removed from an in-service pipeline. Thus, a portable inspection system 30 can be moved to a desired location on a trailer 32. Inspection of the pipeline 34 is accomplished by coiled tubing 36 which is provided with the MFL module 40. The inspection system 30 of in-service gas distribution pipelines 34 is more fully described as follows.

Figure 2:
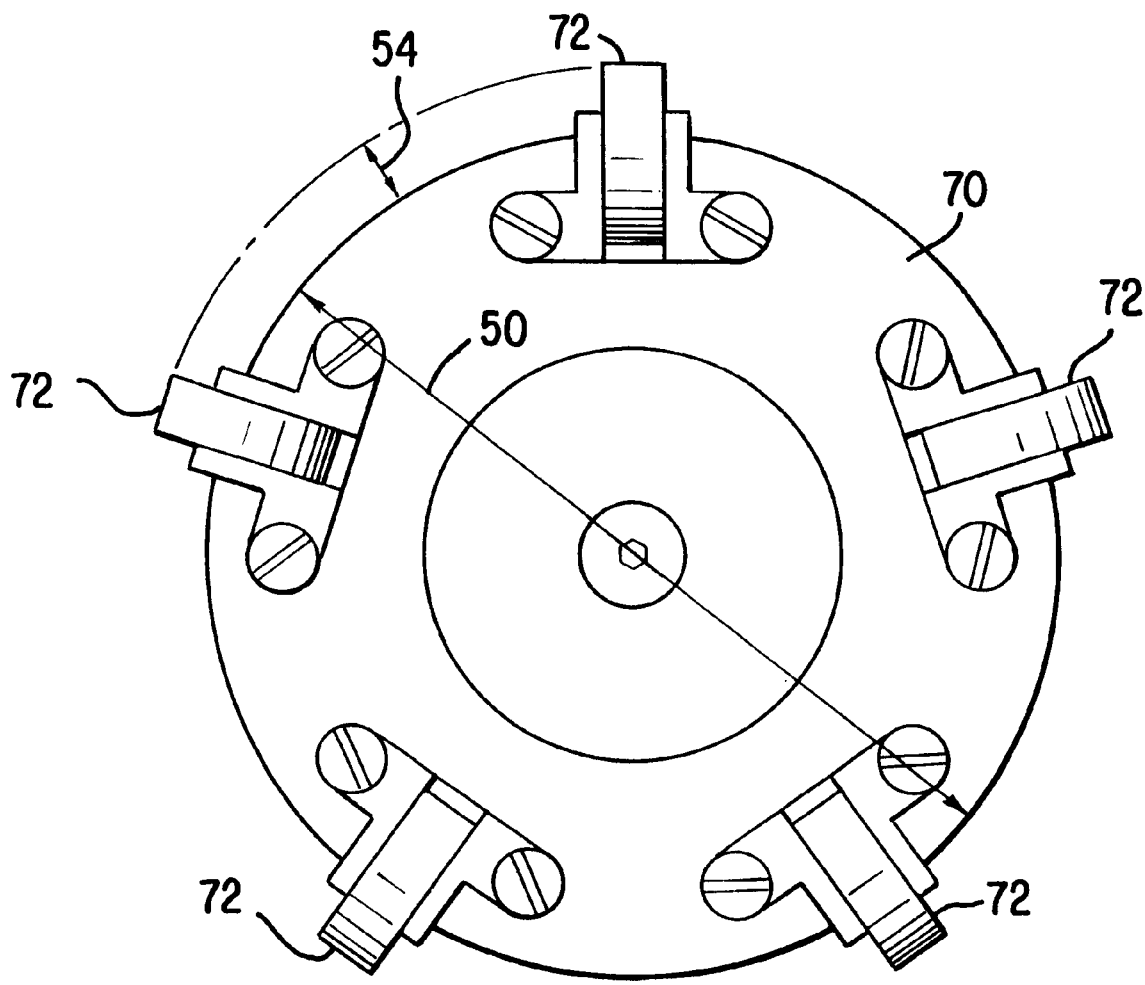
FIG. 2 is a cross-sectional view illustrating a magnetic flux leakage module as incorporated into a preferred embodiment of a system for inspecting in-service gas distribution mains.
Figure 3:
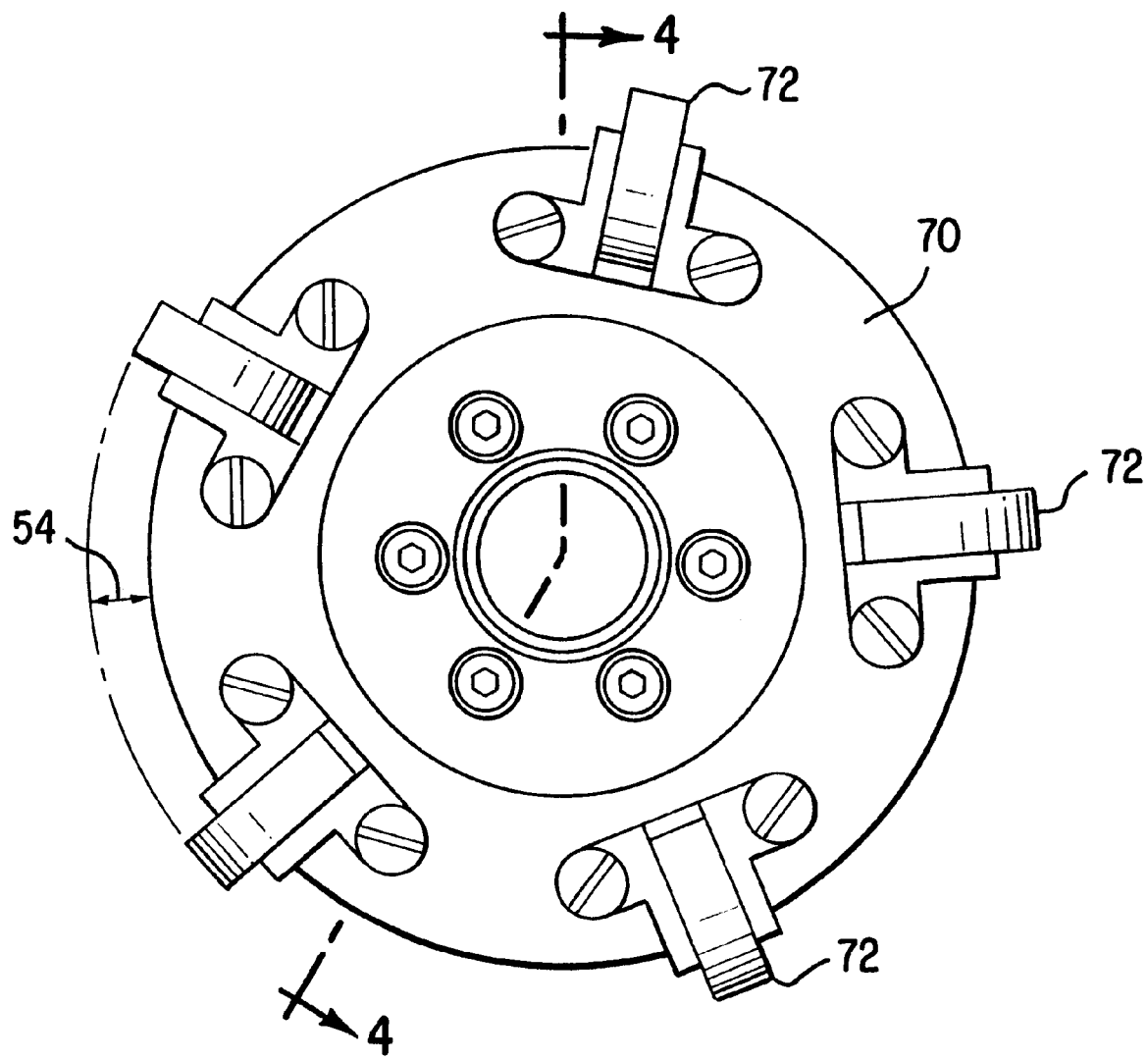
FIG. 3 is a side, cut-away view of the apparatus shown in FIG. 2.
Figure 4:
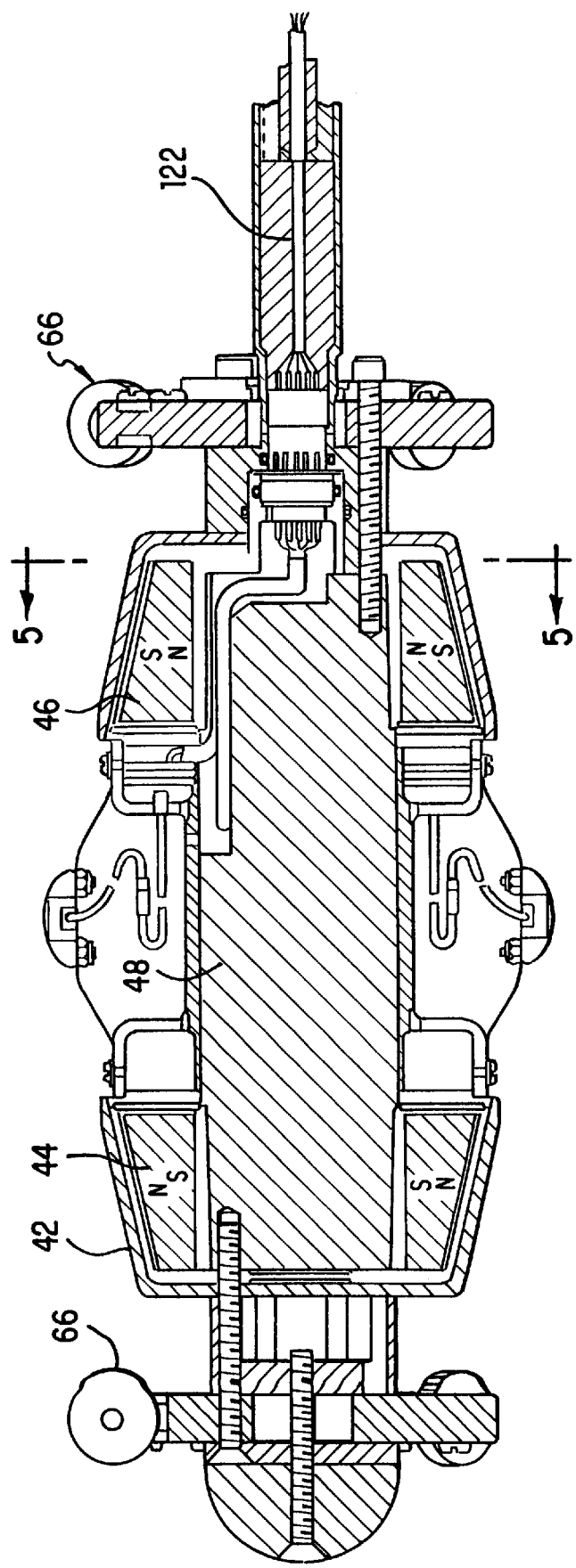
FIG. 4 is a cross-sectional view of the apparatus shown in FIG. 3 as seen along the line 4—4.

Referring now to FIGS. 2 through 4, the MFL sensor module 40 is shown in more detail. The magnet assembly 42 comprises a Magnet N out 44, a Magnet S out 46 and a core 48. The magnet diameter 50 is approximately one inch smaller than that of the pipe 34 to be inspected. The magnetic circuit must operate through the ½ inch radial air gap 54 thus defined.

The air gap 54 is preferred for two reasons. First, it eliminates scraping of the magnet 50 with the pipe wall, as is commonly experienced when applying this technology. This, in turn, reduces contamination of the product with debris which may reside on the inside pipe surface. Second, this air gap 54 allows the product to by-pass the module 40, thereby maintaining throughput.

Figure 5:
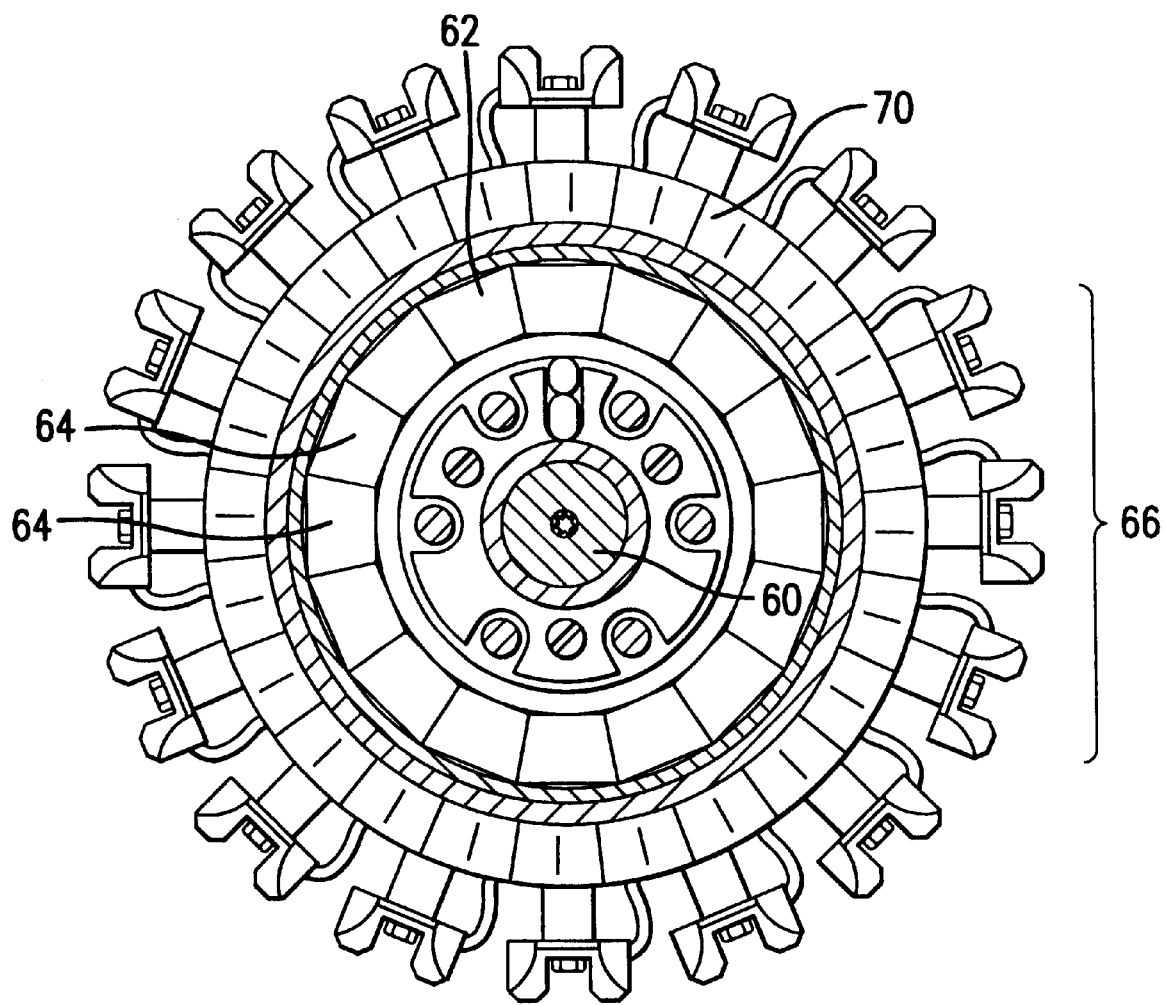
FIG. 5 is a cross-sectional view of the apparatus shown in FIG. 4 as seen along the line 5—5.

To provide a sufficient magnetic circuit, Neodymium-Iron Boron with an energy product of 45 megagauss-orsteds and core 60 of permandure was selected as the magnet material. Permandure is a special steel for magnetic application. Each magnet assembly 42 comprises an array 62 of individual magnets 64 as shown in FIG. 5. This array 62 provides an efficient method of packing the magnets 64 to generate the very powerful magnetic field desired. The magnets 64 are machined in an unmagnetized state. They are then magnetized and assembled. The conical shape of the magnets 64 in this assembly 62 permits the unit 40 to negotiate tighter bends than would be possible with a cylindrical assembly.

Since the magnets 64 do not contact the wall of the pipe, a centering mechanism 66 holds the assembly 40 on the pipe centerline. The centering mechanism 66 permits product bypass and minimizes removal of surface debris. This mechanism 66 is illustrated in FIGS. 4 and 5, at either end of the magnet assembly 42. The centering mechanism 66 must be sufficiently strong to withstand the substantial magnetic forces and yet sufficiently flexible to negotiate bore changes, traverse welds and negotiate bends. Preferably, the mechanism 66 will also permit product by-pass, debris removal and yet add only a minimum of overall length to the assembly 40.

The centering mechanism thus comprises a flexible urethane disk 70 with a diameter equal to the magnet diameter, to permit maximum product by-pass. Five equi-space wheels 72 are mounted on the disk 70. The wheels 72 roll on the inside surface of the pipe to minimize debris removal and the urethane provides flexibility to the disk 70 to negotiate bore changes. Spring rates are selectable by changing the cross section of the disk 70.

Figure 6:
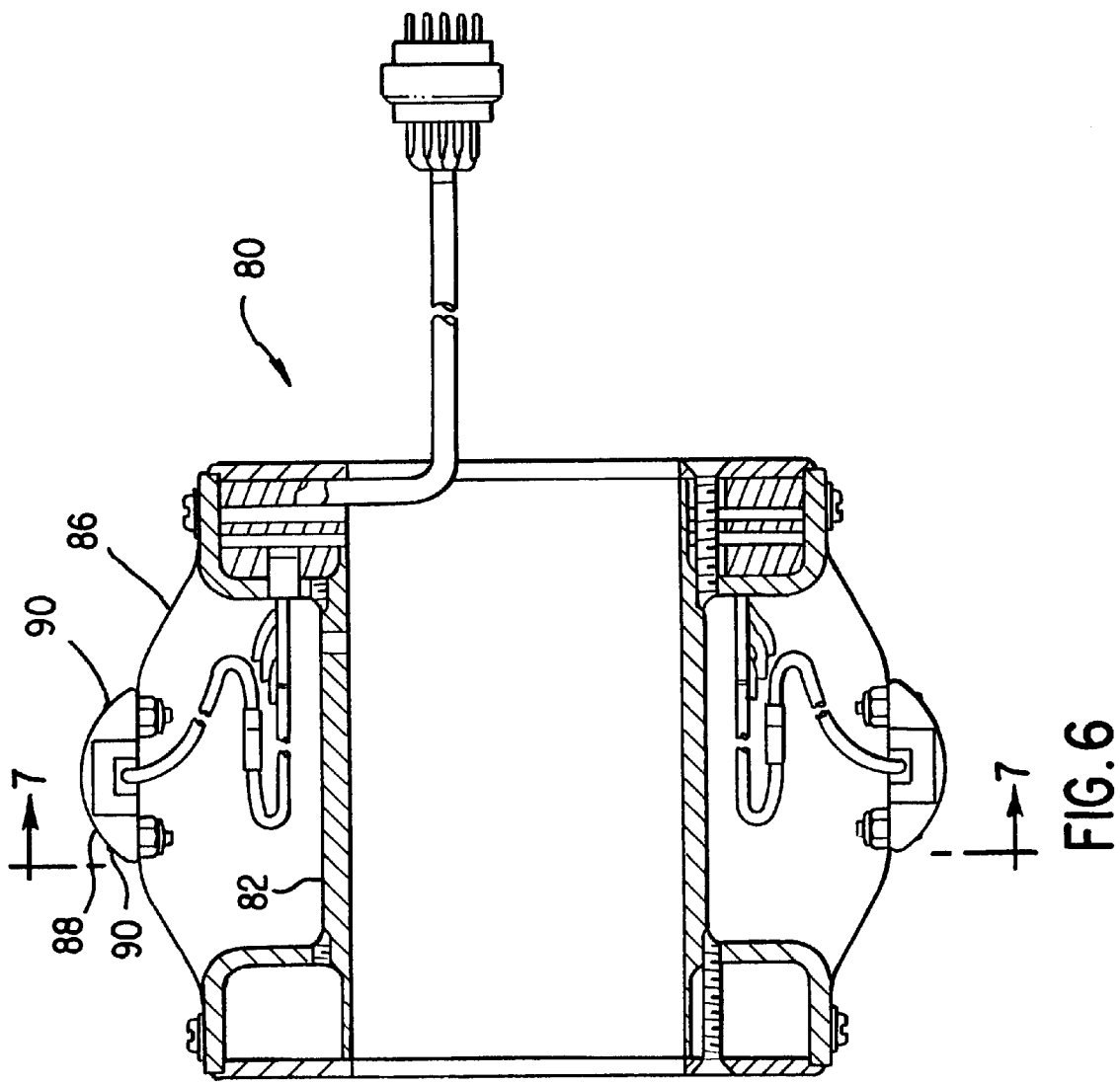
FIG. 6 is a side, cut-away view illustrating a magnetic sensor subassembly of a preferred embodiment of a system for inspecting in-service gas distribution mains.
Figure 7:
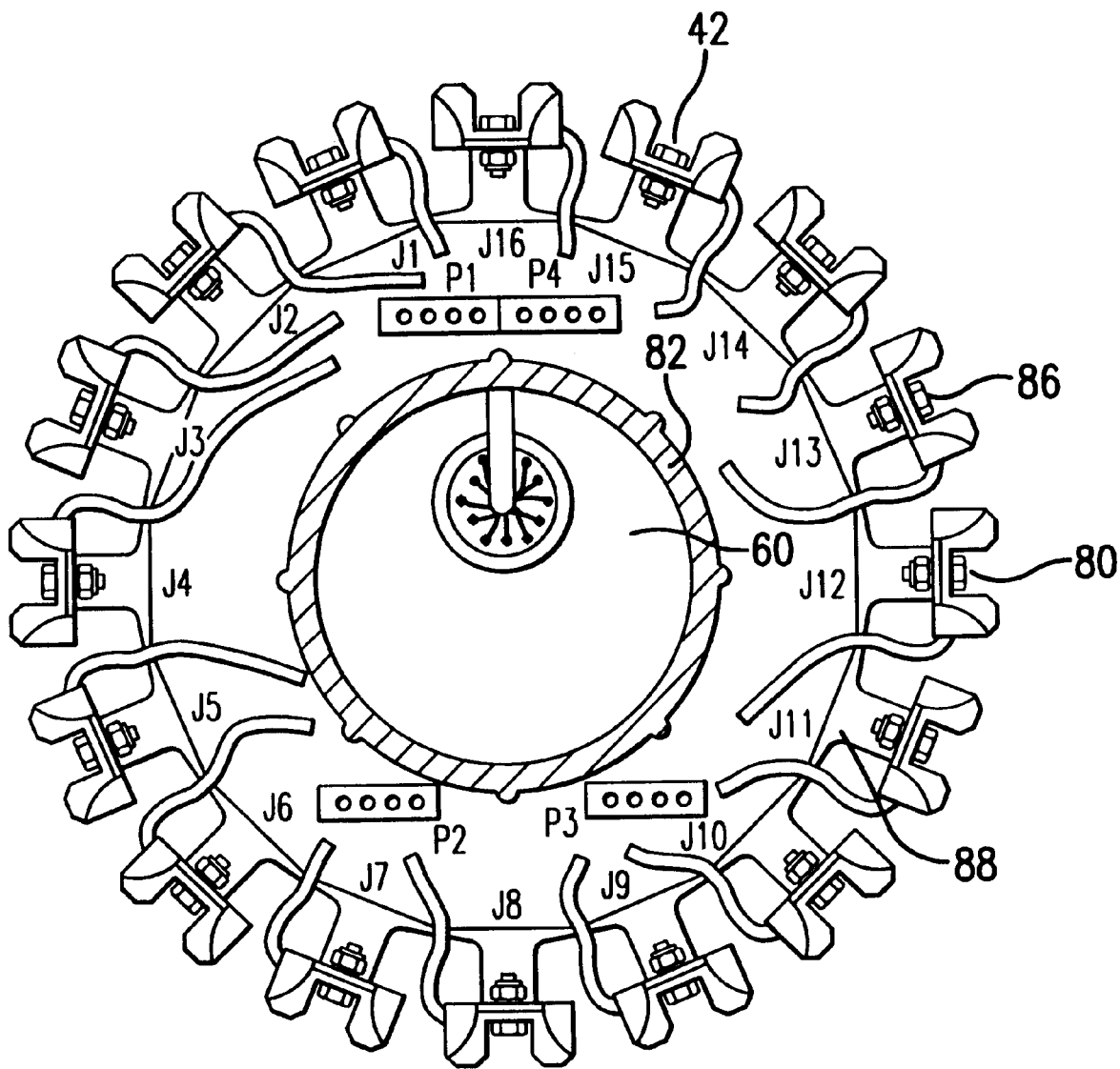
FIG. 7 is a cross-sectional view of the apparatus shown in FIG. 6 as seen along the line 7—7.

As shown in FIGS. 6 and 7, the sensor array 62 and processing subassembly 80 is positioned between the magnet poles 44, 46. The subassembly 80 comprises a stainless steel (non-magnetic) spool 82 which slides over the permandure core 60 and is maintained in place by the magnet assemblies 42. Radiating circumferentially around the spool 82 are sixteen spring mounts 86 each containing a sensor housing 88. Each sensor housing 88 contains two sensor elements 90 for a total of thirty-two circumferentially, equi-spaced sensor elements 90. This high density sensor array 62 collects precise magnetic data. In the preferred embodiment, the sensors 90 are integrated Hall elements (HGT 2100), currently available from Lake Shore Cryotronics of Westerville, Ohio, having preferred sensitivity and low operating current.

The mounting springs 86 permit bi-directional operation and apply minimum pressure to the sensor housing 88, which preferably can slide smoothly along the pipe wall and allow maximum product by-pass. The sensor housing 88 provides a two point contact with the pipe wall to improve stability and minimize abrasion.

Figure 8:
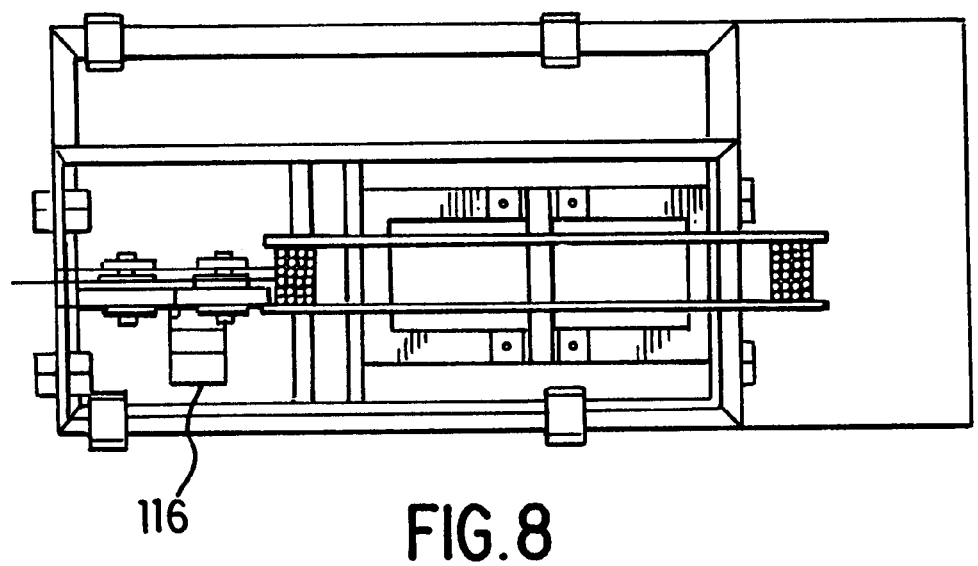
FIG. 8 is a top plan view illustrating a tubing delivery system of a preferred embodiment of a system for inspecting in-service gas distribution mains.
Figure 9:
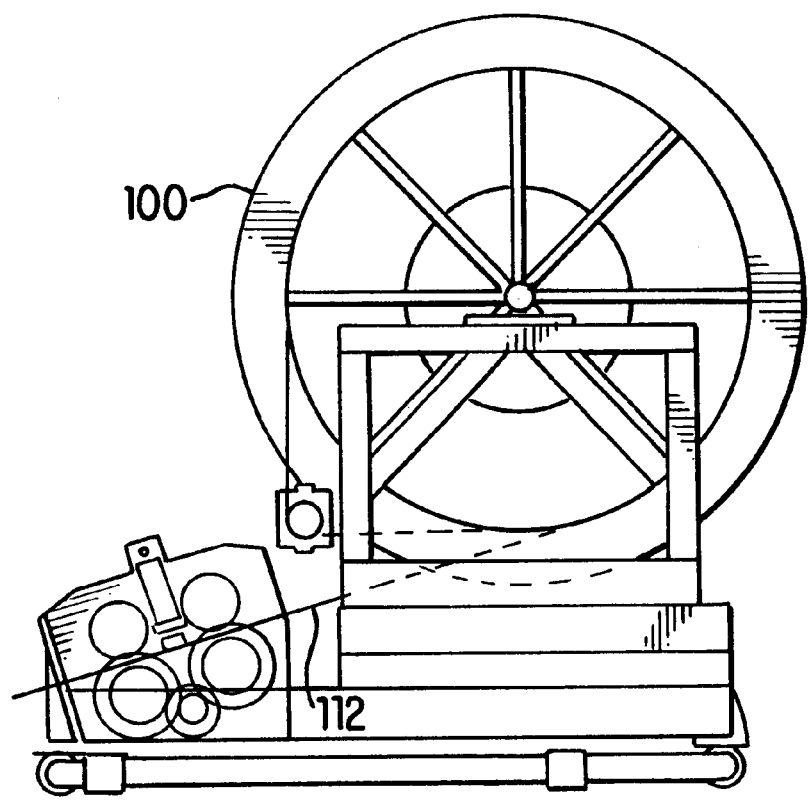
FIG. 9 is a side plan view of the apparatus shown in FIG. 8.
Figure 10:
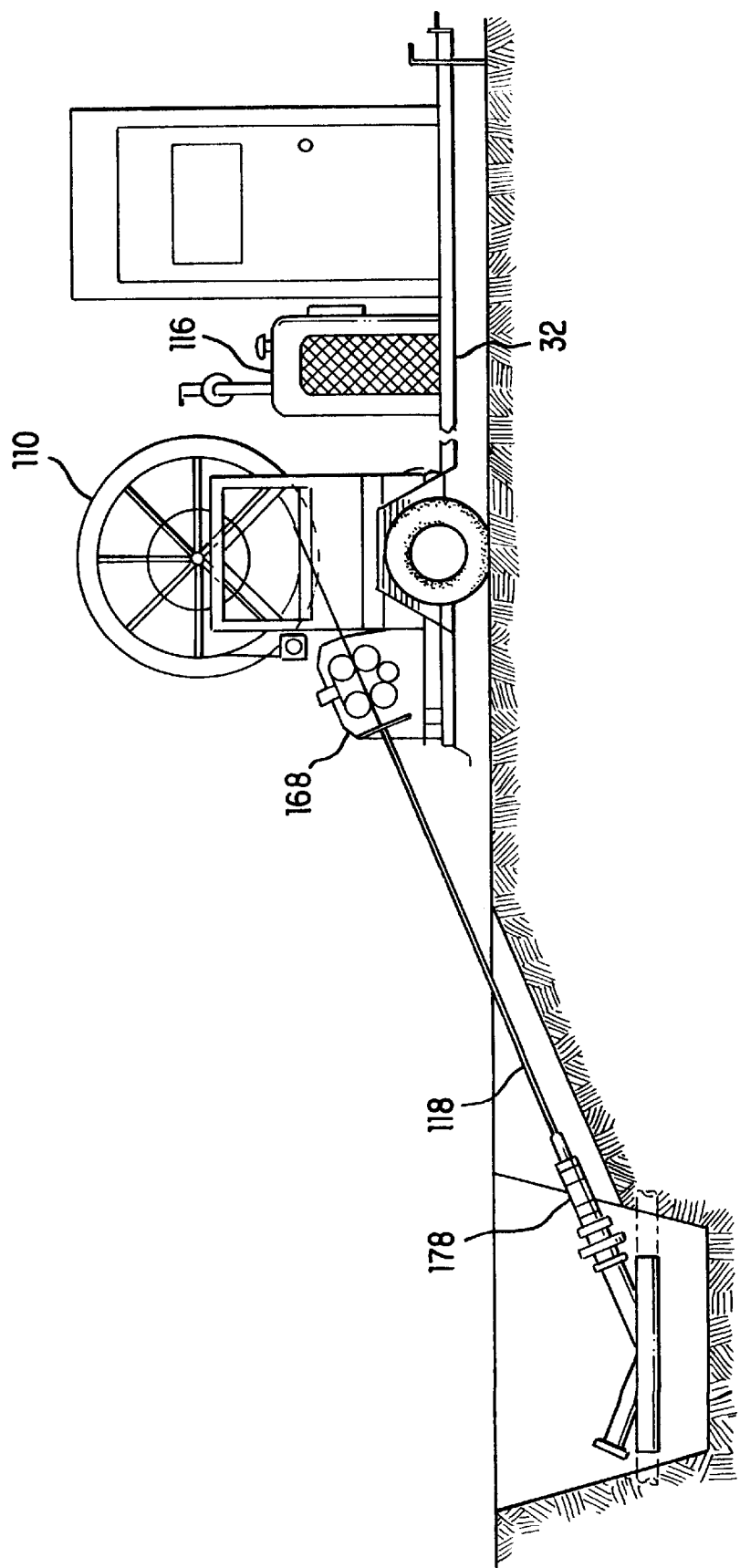
FIG. 10 is a side plan view illustrating a portion of a preferred embodiment of a system for accessing and inspecting in-service gas distribution mains.

To understand the design parameters of the data acquisition system, it is necessary to assess the means for propelling the inspection module 40 through the pipeline. Since the pressure and flow in the pipeline are inadequate to propel the tool 40 conventionally, an alternative propulsion structure 100 is provided. As shown in FIGS. 8 and 9, coiled tubing 112 is provided. A spool 110 of tubing 112 is typically constructed of stainless steel or composite rod, and can be pushed or pulled through pipe 34 by a hydraulic power unit 116.

To provide real time analyses, the magnetic inspection module 40 is electrically and mechanically linked to data acquisition systems above ground by a flexible tube member 118. Conductors 122 (shown in FIG. 4) are contained within the tube 112, and conduct data from the sensors electronic processing cards (not shown) to the above-ground data acquisition computer (not shown), and power the sensors 90, as well. As described above, the module 40 contains thirty-two sensors 90. Each sensor 90 is a 4-terminal "bare" element wherein two conductors are required for DC bias and two conductors are required for signal. The signal outputs are preferably buffered and amplified before further processing, thereby necessitating providing a printed circuit card having thirty-two buffer amplifiers. Rather than handle each sensor individually, which would require at least thirty-two conductors for sensor signals and additional conductors for power and signal ground, a more efficient structure is provided.

By adding a second printed circuit card, all thirty-two buffer outputs are fed into a 32 channel multiplexer. Each channel is selected in turn, and all sensor channels are thereby transmitted through a single conductor. An address generator is provided which is strobed from the data acquisition computer. When the address generator receives a strobe pulse, it accesses each sensor channel in turn and sends the selected signal to an amplifier, which then transmits the signal through the conductor to a analog-to-digital converter located in the data acquisition computer. When all thirty-two channels are accessed, the system waits for the next strobe. The strobe signal is generated by a transducer driver by the movement of the delivery tube. This then gives sensor data which is proportional to distance which can, in turn, be used to provide a distance measurement for locating and measuring features or defects detected. Thus, only 5 conductors (2 power, 1 strobe, 1 signal, 1 utility) are required.

Next, the delivery system 100 is described. As seen in FIGS. 8 through 13, the coiled tubing delivery hardware 100 is mounted on a trailer 32 and placed at the edge of the pit excavation. The trailer 32 is fitted with a hydraulic pump 116 to operate the coiled tubing injector 168. The trailer 32 is further fitted with an electrical generator (not shown) to supply power to the MFL inspection system 30 electronics.

Figure 13:
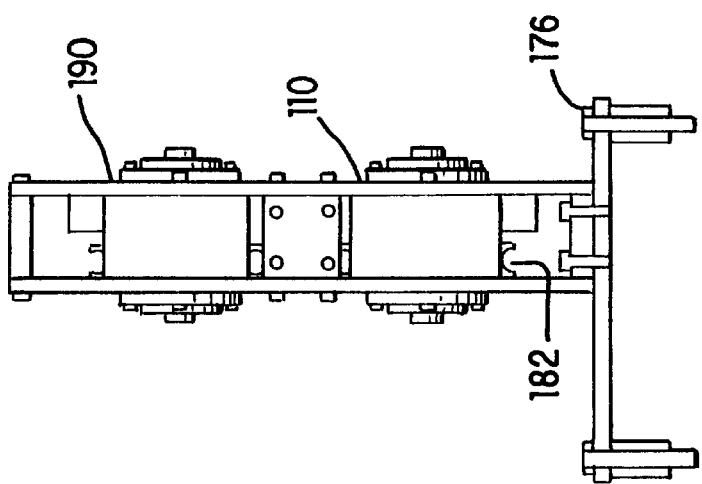
FIG. 13 is a frontal plan view illustrating the apparatus as shown in FIGS. 11 and 12.
Figure 11:
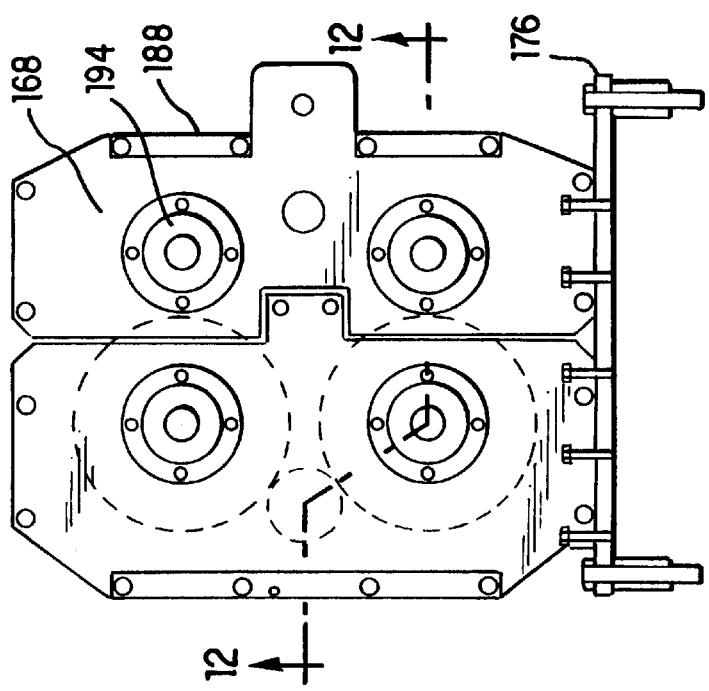
FIG. 11 is a side, cut-away view illustrating a coiled tubing injection assembly of a preferred embodiment of a system for inspecting in-service gas distribution mains.
Figure 12:
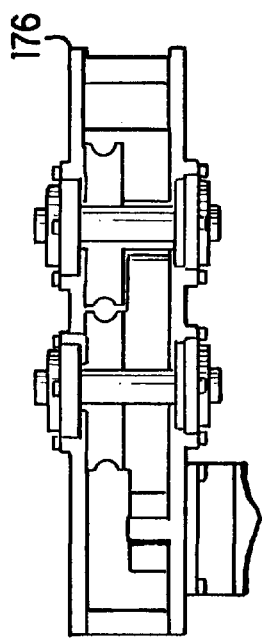
FIG. 12 is a top plan view illustrating the apparatus shown in FIG. 11 as seen along the line 12—12.

The rear of the trailer 34 is fitted with two different types of delivery: (1) the primary steel coiled tubing for inspecting long runs of gas mains 34 in the majority of applications, and (2) secondary fiberglass rod/cable composite for performing inspection through highly-deviated sections of pipe 34. The spool 110 is mounted to a piston controlled slide frame 176 (as shown in FIGS. 11 through 13). The slide frame 176 provides both side-to-side and front-to-back precise positioning, thereby providing adjustment of the coiled tubing injector head 178 over the gas main 34. The design provides one foot left-to-right adjustment and one foot front-to-back adjustment. The spool 110 features a level wind control 182 to assure correct spooling of the tubing 112 onto the spool 110. The tubing 112 is pushed or pulled into the gas main 34 using a coiled tubing injector 168 which comprises a bi-directional roller assembly 188 shown in FIGS. 11 through 13.

A second spool 190 comprises a composite push rod/cable assembly which provides a secondary delivery means for inspecting gas mains having bend radii which cannot be negotiated by the steel coiled tubing 112 without exceeding the tubing yield limit. The composite tubing 112 is directed through an injector assembly 168 having powered rollers 194 having a profile which effectively grips the tubing 112 without crushing it. These rollers 194 are driven by a hydraulic motor (not shown) mounted on the injector assembly 168. Thus, the inspection module 40 can be moved through the pipe 34 and retrieved from a single access point.

As illustrated by FIGS. 14 through 19, insertion techniques and hardware are disclosed which enable gaining access to the in-service pipeline 34, performing the MFL inspection process and restoring the gas main to its original strength. A template 202 or weld-on clamp is preferably attached to the existing gas main 34 to provide a platform for inspection and restoration operations. Attaching the template 202 requires full circumferential excavation around the gas main 34. The two halves 204 of a split template assembly 202 are welded onto steel gas mains or bolted onto cast iron mains. Full encirclement of the main 34 is preferred.

In the preferred embodiment, the template 202 comprises a top assembly 208 fitted with one or two short length wye entry tubes 210 at a 15 to 20 degree angle to the main 34 and a lower section 212 which fits directly onto the main 34. These two elements 210, 212 are welded to the main 34 prior to cutting the access hole(s) 214. A flange assembly 216 is attached to the top of each wye tube 210 for subsequent attachment of a full bore gate valve 218 and for sealing the gas main 34 after the inspection is completed. The 20 degree wye fittings 210 are pre-made onto the top template 202. The only field welding comprises two linear welds joining the sides of the template 202 to each other and to the gas main 34, and two circumferential welds at the ends of the template 202. The height of the left-in-place template 202 is 8 inches above the main 34, which should pose no operational problems.

The template 202 provides superior support to the gas main 34 due to its longer bearing length. Since the template is installed prior to drilling the hole, all bending stresses in the main will be absorbed by the template mounting. Consequently, no residual stresses will be present to deform the pipe when the original material is weakened by cutting. Thus, the total template bearing length provides enough stiffness to counter the reduced stiffness at the cut location.

Figure 20:
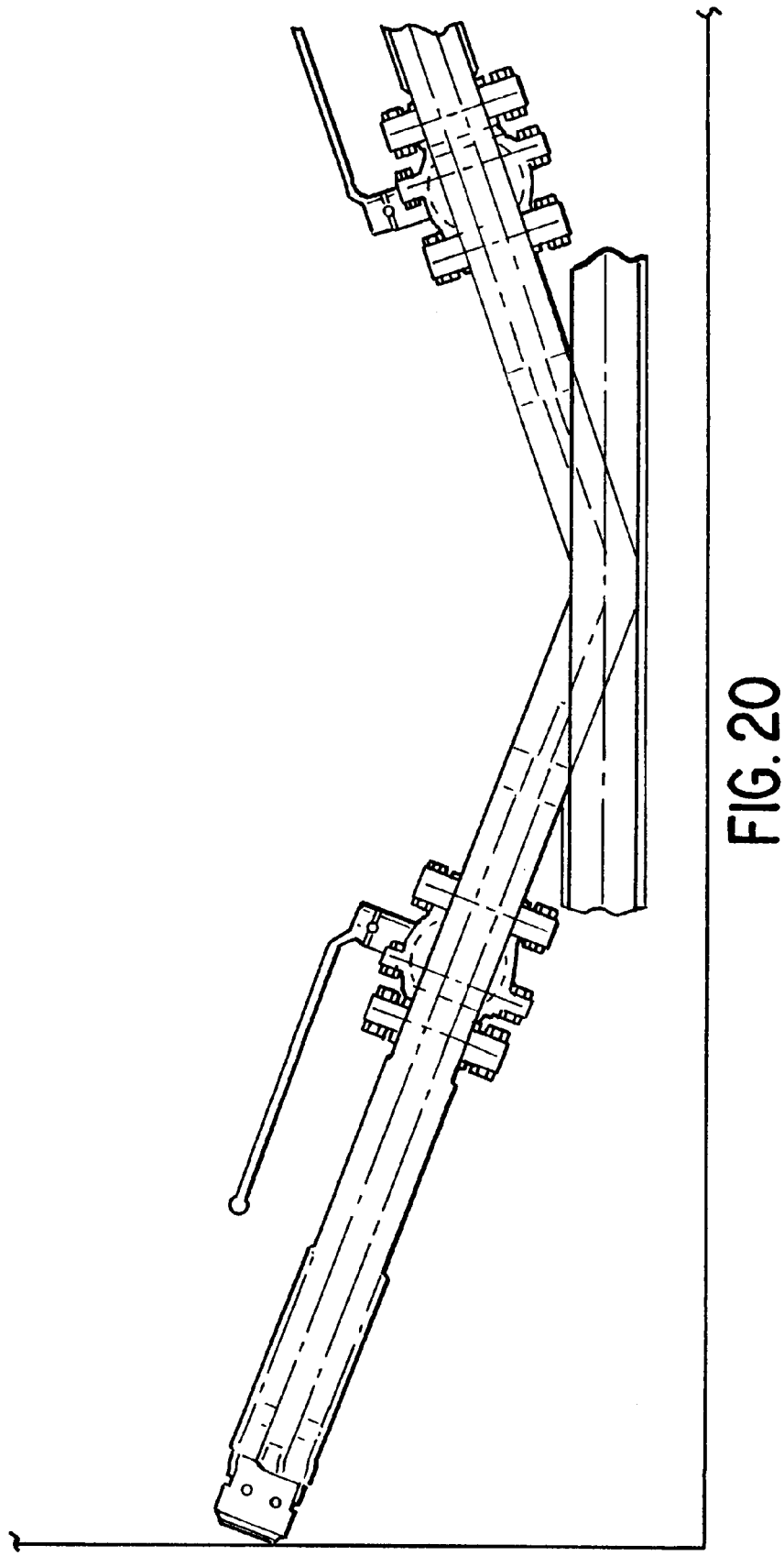
FIG. 20 is a side, cut-away view illustrating a portion of a preferred embodiment of a system for inspecting in-service gas distribution mains showing dual risers for non-intersecting holes.
Figure 21:
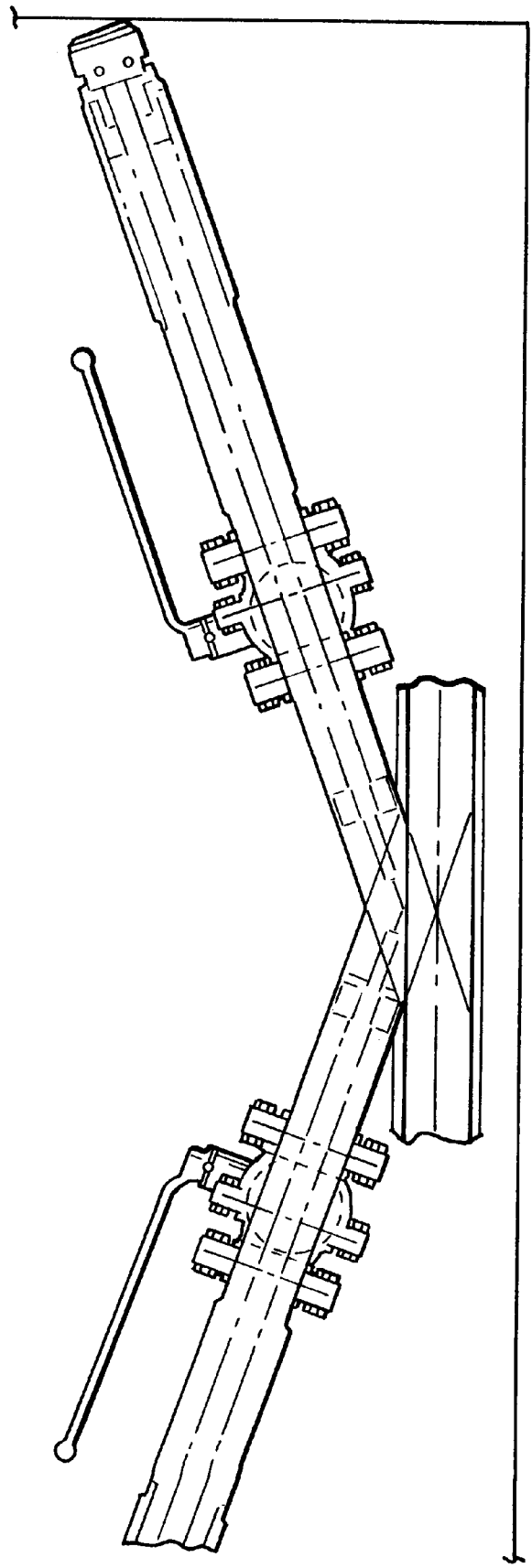
FIG. 21 is a side, cut-away view illustrating a portion of a preferred embodiment of a system for inspecting in-service gas distribution mains showing dual risers for intersecting holes.
Figure 22:
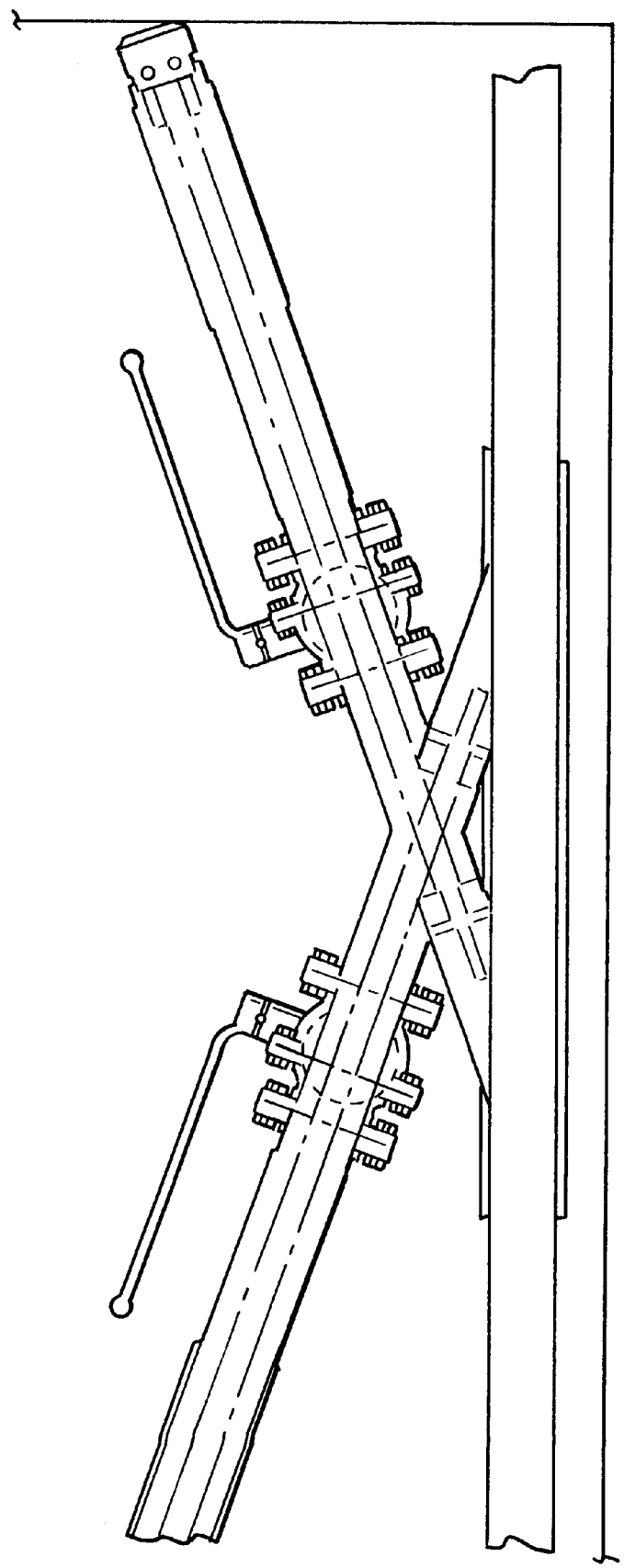
FIG. 22 is a side, cut-away view illustrating a portion of a preferred embodiment of a system for inspecting in-service gas distribution mains showing dual intersecting risers for non-intersecting holes.

As shown in FIGS. 20 through 22, three entry variations are available to effect insertion of the module. The first of these, dual risers for use with nonintersecting holes, is shown in FIG. 20. The holes do not intersect so each is drilled independent of the other. Drilling single holes has no known impact on hole saw life and assures consistent retrieval of the coupon. This application is 39 inches long and requires an excavation of 10.4 feet in length to inspect a 3 ft. deep gas main.

As shown in FIG. 21, dual riser for use with intersecting holes can be utilized. The two holes intersect at a 20 degree incident angle. The impact of the hole shape and interrupted cut on the operating life of the hole saw and the ability to successfully remove the second, irregularly-shaped coupon must be determined. However, if appropriate to the situation, this approach reduces the excavation length to 9.3 feet.

Finally, as shown in FIG. 22, dual intersecting risers for use with nonintersecting holes can be employed. This is the preferred method where possible, as it incorporates the reduction in pit length made possible by intersection while avoiding coupon removal and cutter life issues. The fixture measures 48 inches in length and requires a pit length of 8.5 feet to perform bi-directional inspection of a gas main buried 3 feet deep.

Figure 14:
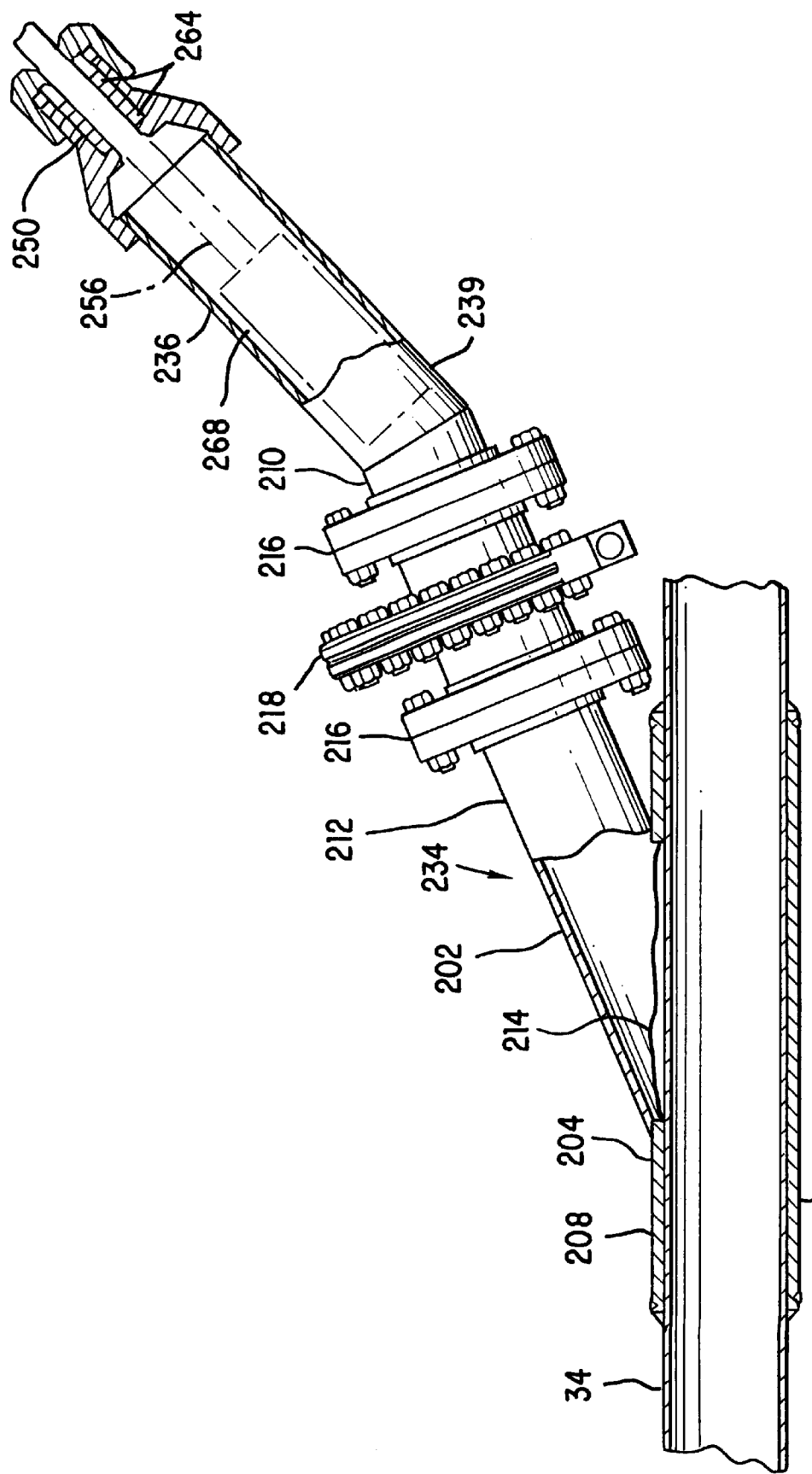
FIG. 14 is a side, cut-away view illustrating a MFL launch assembly of a preferred embodiment of a system for inspecting in-service gas distribution mains.
Figure 15:
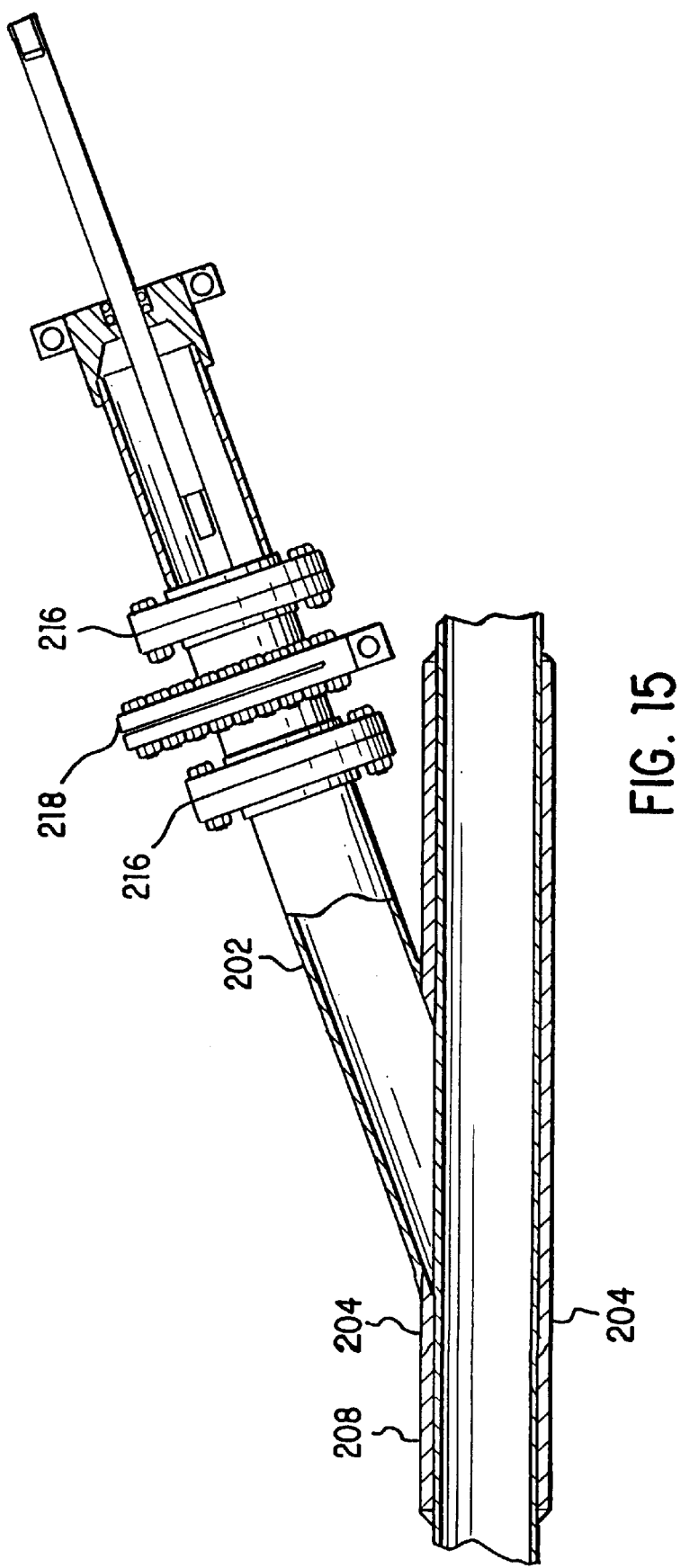
FIG. 15 is a side, cut-away view illustrating a MFL launch assembly showing the initial hole saw installation of a preferred embodiment of a system for inspecting in-service gas distribution mains.
Figure 16:
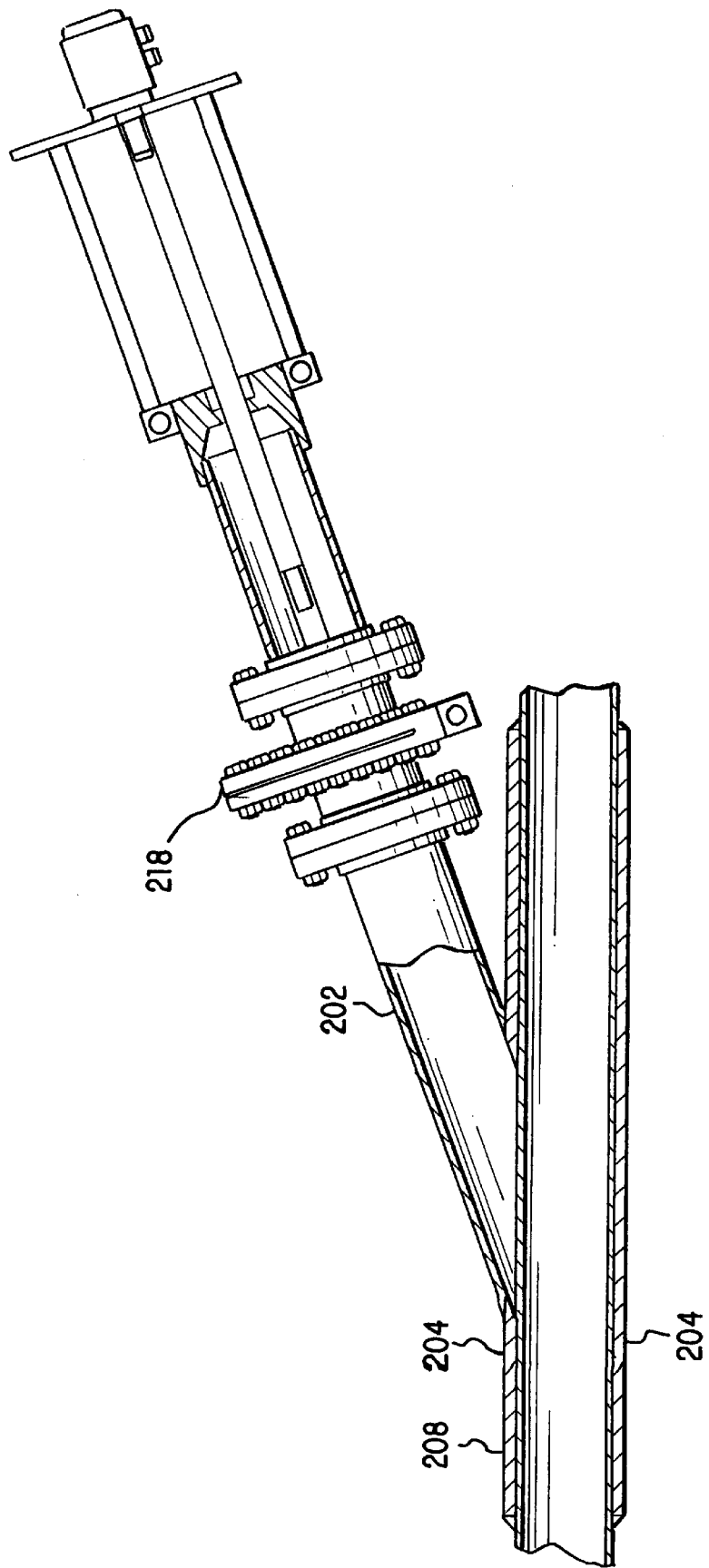
FIG. 16 is a side, cut-away view illustrating a MFL launch assembly as seen during a drilling process of a preferred embodiment of a system for inspecting in-service gas distribution mains.

In order to perform all operations under no-blow conditions, a full opening valve 214 should be placed in the riser assembly 234 as shown in FIG. 14. This valve 214 should have a bore diameter large enough to allow the MFL inspection device 40 to pass through. A 4 inch fully opening gate or ball valve is employed for applications in 4 inch mains. The valve 214 is closed while tools are being placed into or removed from the assembly 30. The valve 214 is attached to the template/launch tube assembly 236 with flanges 216 and is removed when the inspection is complete.

To minimize the pit length requirements for the assembly, a 22.5 degree transition fitting 239 can be placed directly above the valve 214 (after the valve 214 has been closed) for the inspection operation. This requires a pit length between 8.5 to 10 feet to perform 2-way inspection of a buried gas main. Using template 202 accommodates a greater variety of inspection methodologies than other methods. The template 202 allows passage of larger inspection heads and sensor packages.

A packing seal 250 is employed above the full bore gate valve 214 to seal around the coiled tubing conveyance member 256 or the drill stem 258 of the hole saw assembly (not shown). The packing 250 preferably provides a leak free seal but does not cause excessive friction (drag) on the conveyance tubing. Wear rings 264 are located at both ends of the packing material to protect against wear and maximize operating life. The packing 250 now becomes the primary seal of the natural gas at this point. Upon completion of the operation, the MFL inspection device 40 is pulled back into the launch chamber 268 and the valve 214 closed. The inspection device 40 can then be removed.

Preferably, steel and cast iron gas mains are accessed using commercial bi-metal hole saws as the cutting element. Bi-metal hole saws cut a very narrow kerf and therefore remove very little material. This results in very high drilling rates as well as minimal horsepower requirements. Additionally, the cost of the hole saws is very low, permitting use of a new hole saw in each new application.

In one embodiment, the hole saw contacts the gas main 34 at an angle. The minimum angle required to use steel tubing is a 20 degree template riser angle in 4" mains. The hole saw assembly is powered by hydraulics. The motor is coupled to the bi-metal hole saw by a drive shaft assembly. Bit weight is applied to the hole saw by connecting a manual jack screw to the hydraulic motor body. This design allows the operator direct tactile response for how much bit load to apply. It also prevents breakage of the hole saw.

Once the inspection has been completed, the MFL inspection device 40 is removed from the riser 234 with the valve 214 closed. The template 202 is designed to be left in place and can be re-entered at a later date when follow-up inspection is desired. To remove the lower valve, the template riser should first be sealed so that no gas escapes. This is accomplished by setting an expandable plug in the bore of the riser before removing the valve. The setting assembly requires the same hardware as the hole saw assembly with the exception that the bit load mechanism is removed. A long-handle setting tool is used to manually expand the plug. Once the plug is set, the operator can remove the valve and close the template riser with a blind seal flange. The blind seal flange provides a second, redundant seal and enables the main to be re-entered in the future without blowing gas because it allows attachment of the gate valve/launch tube assembly prior to the removal of the expandable seal plug.

Thus, a system for inspecting in-service gas distribution mains is disclosed. A sensor module for use in a system for inspecting in-service gas distribution mains comprises a plurality of magnet assemblies each having a Magnet N out, a Magnet S out and a magnet core, the magnet assemblies being conical in shape and being arranged into a circular array. The magnet array diameter is smaller than that of a pipe to be inspected, thus defining a radial air gap. The magnet array being constructed and arranged to provide a magnetic circuit having sufficient strength so as to be operable through the radial air gap. A centering mechanism is constructed and arranged to maintain the sensor module in concentric relation with the pipe to be inspected.

The centering mechanism comprises a flexible disk having a diameter approximately equal to the magnet array diameter and a plurality of wheels mounted in fixed relation to the disk. The flexible disk is constructed urethane and constructed and arranged to provide sufficient flexibility to the disk to permit the sensor module to negotiate bore changes in the pipe to be inspected. The wheels are arranged in radially symmetric, spaced apart relation and disposed outwardly away from the center of the disk. The outermost extension of the wheels thereby defines an outer working diameter which is slightly less than but approximately equal to the inner diameter of the pipe to be inspected.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A sensor module for use in a system for inspecting in-service gas distribution mains comprising:
   a plurality of magnet assemblies each having a Magnet N out, a Magnet S out and a magnet core, the magnet assemblies being conical in shape and being arranged into a circular magnet array;
   a diameter of the magnet array being smaller than an inner diameter of a pipe to be inspected, thus defining a radial air gap;
   the magnet array being constructed and arranged to provide a magnetic circuit having sufficient strength so as to be operable through the radial air gap;
   a processing subassembly positioned around the magnet core, the processing subassembly comprising a plurality of sensor elements fixedly positioned around a circumference of the processing subassembly, each sensor element contacting an inner surface of the pipe; and
   a centering mechanism constructed and arranged to maintain the sensor module in concentric relation with the pipe to be inspected.

2. A sensor module as set forth in claim 1, wherein the centering mechanism comprises a flexible disk having a diameter approximately equal to the magnet array diameter and a plurality of wheels mounted in fixed relation to the disk.

3. A sensor module as set forth in claim 2, wherein the wheels are arranged in radially symmetric, spaced apart relation and disposed outwardly away from the center of the disk; the outermost extension of the wheels thereby defining an outer working diameter; the outer working diameter being slightly less than but approximately equal to the inner diameter of the pipe to be inspected.

4. A sensor module as set forth in claim 2, wherein the flexible disk is constructed of a material selected to provide sufficient flexibility to the disk to permit the sensor module to negotiate bore changes in the pipe to be inspected.

5. A sensor module as set forth in claim 4, wherein the flexible disk is constructed of urethane.

6. A sensor module as set forth in claim 3, wherein the flexible disk is constructed of a material selected to provide sufficient flexibility to the disk to permit the sensor module to negotiate bore changes in the pipe to be inspected.

7. A sensor module as set forth in claim 6, wherein the flexible disk is constructed of urethane.

8. A sensor module for use in a system for inspecting in-service gas distribution mains comprising:
   a plurality of magnet assemblies each having a Magnet N out, a Magnet S out and a magnet core, the magnet assemblies being conical in shape and being arranged into a circular magnet array;
   a diameter of the magnet array being smaller than an inner diameter of a pipe to be inspected, thus defining a radial air gap;

the magnet array being constructed and arranged to provide a magnetic circuit having sufficient strength so as to be operable through the radial air gap;

a processing subassembly positioned between the Magnet N out and the Magnet S out;

a plurality of equi-spaced spring mounts radiating circumferentially around the processing subassembly, each spring mount having a sensor housing containing two sensor elements;

a centering mechanism constructed and arranged to maintain the sensor module in concentric relation with the pipe to be inspected, the centering mechanism comprising a flexible disk having a diameter approximately equal to the magnet array diameter and a plurality of wheels mounted in fixed relation to the disk, the flexible disk being constructed of urethane and constructed and arranged to provide sufficient flexibility to the disk to permit the sensor module to negotiate bore changes in the pipe to be inspected; and the wheels being arranged in radially symmetric, spaced apart relation and disposed outwardly away from the center of the disk; the outermost extension of the wheels thereby defining an outer working diameter; the outer working diameter being slightly less than but approximately equal to the inner diameter of the pipe to be inspected.

9. A sensor module for use in a system for inspecting an in-service gas distribution pipeline comprising:

a magnet assembly having a plurality of individual magnets arranged in a circular array, the magnet assembly having a conical shape and further comprising a Magnet N out, a Magnet S out and a core;

at least one centering mechanism connected to an end portion of the magnet assembly, the at least one centering mechanism arranged to maintain the sensor module in axial alignment with a centerline of the pipeline; and a processing subassembly positioned between the Magnet N out and the Magnet S out, the processing subassembly comprising a plurality of sensor elements fixedly positioned around a circumference of the processing subassembly.

10. A sensor module as set forth in claim 9, wherein each sensor element contacts an inner surface of the pipeline.

11. A sensor module as set forth in claim 9, wherein the processing subassembly further comprises a spool positioned around the core, the spool having a plurality of spring mounts, each spring mount having a sensor housing for containing two sensor elements.

12. A sensor module as set forth in claim 9, wherein the sensor elements are equi-spaced around the circumference of the processing subassembly.

13. A sensor module as set forth in claim 9, wherein the magnet assembly has a diameter smaller than a diameter of the pipeline, an outer surface of the magnet assembly and an inner surface of the pipeline defining a radial air gap.

14. A sensor module as set forth in claim 13, wherein the magnet assembly provides a magnetic circuit having sufficient strength so as to be operable through the radial air gap.

15. A sensor module as set forth in claim 9, wherein the Magnet N out and the Magnet S out comprise Neodymium-Iron Boron with an energy product of 45 megagauss-orsteds and the core comprises permandure.

16. A sensor module as set forth in claim 9, further comprising a second centering mechanism connected to a second end portion of the magnet assembly, the first centering mechanism and the second centering mechanism arranged to maintain the sensor module in axial alignment with a centerline of the pipeline.

17. A sensor module as set forth in claim 9, wherein the sensor module is moveable along a centerline of the pipeline in two directions.

18. A sensor module as set forth in claim 9, wherein the sensor module comprises thirty-two circumferentially, equi-spaced sensor elements.

* * * * *